United States Patent
Taricco

Patent Number: 5,447,700
Date of Patent: Sep. 5, 1995

[54] AUTOCLAVE COGENERATION SYSTEM

[75] Inventor: Todd Taricco, Zephyr Cove, Nev.

[73] Assignee: Thermal Equipment Corporation, Torrance, Calif.

[21] Appl. No.: 196,691

[22] Filed: Feb. 10, 1994

[51] Int. Cl.$^6$ ............................................. A61L 2/06
[52] U.S. Cl. ................................. 422/295; 422/292; 422/305; 422/307
[58] Field of Search ............... 422/305, 307, 308, 295, 422/200, 292; 60/39.02, 39.07; 34/86, 513, 514

[56] References Cited

U.S. PATENT DOCUMENTS

| | | | |
|---|---|---|---|
| 3,966,407 | 6/1976 | Zuckerberg et al. | 422/307 X |
| 4,052,858 | 10/1977 | Jeppson | 60/648 |
| 4,092,111 | 5/1978 | Gaignonx et al. | 422/198 |
| 4,119,400 | 10/1978 | Kurz | 422/298 |
| 5,122,318 | 6/1992 | Bonet et al. | 264/85 |

Primary Examiner—Robert J. Warden
Assistant Examiner—Krisanne M. Thornton
Attorney, Agent, or Firm—Blakely, Sokoloff, Taylor & Zafman

[57] ABSTRACT

An autoclave system which uses the exhaust gas of a turbine to heat an autoclave. The exhaust gas of the turbine is approximately 1200° F., low enough to be coupled to the heater coils of the autoclave. The output shaft of the turbine may be coupled to a generator that drives the autoclave motor and other subsystems. The output shaft of the turbine may also be coupled, either directly or through the generator, to the compressors of a nitrogen processing plant. The processed nitrogen can be introduced to the autoclave to reduce the risk of fires.

7 Claims, 1 Drawing Sheet

AUTOCLAVE COGENERATION SYSTEM

BACKGROUND OF THE INVENTION

1. Field of the Invention

The present invention relates to an autoclave that is heated by the output gas of a turbine.

2. Description of Related Art

Autoclaves are typically used to form composite parts that contain fibrous material impregnated with a thermosetting organic resin. The composite parts are formed by elevated pressures and temperatures introduced to the inner chamber of the autoclave. Heat is typically supplied to the autoclave by coils which contain a hot gas. The hot gas is conventionally produced by a gas combustion chamber.

Gas combustion chambers generate combusted gas with a temperature of approximately 3200° F. The coils within the autoclave can only withstand temperatures in the range of 1300° F. Temperatures above 1300° F. may cause the coil material to become brittle and rupture when exposed to the pressure of the autoclave. To reduce the temperature of the output gas from the combustion chamber, conventional autoclave systems use excess air to cool the combusted gas. 300% excess air is typically required to create an output gas temperature of 1300° F. Pumping excess air into the combustion chamber lowers the energy efficiency of the chamber.

The excess air is blown into the heater coils, even after the inner chamber of the autoclave has reached the desired elevated temperature. The excess air must be constantly heated to maintain the temperature within the autoclave. This constant heating of the excess air also lowers the efficiency of the overall system. It would be desirable to have a more energy efficient autoclave system.

To prevent catastrophic fires from occurring within an autoclave, it is desirable to fill the autoclave inner chamber with nitrogen. U.S. Pat. No. 5,122,318 issued to Bonet et al, discloses a process for producing nitrogen that is provided to an autoclave. The Bonet patent includes a membrane which creates nitrogen from atmospheric air. The air is pushed through the membrane by a compressor. The Bonet system also contains a second compressor which fills a holding tank with the processed nitrogen. Although effective in producing nitrogen for use in an autoclave, the Bonet process requires additional energy to run the compressors of the system. It would be desirable to have an autoclave system which can utilize the Bonet nitrogen processing plant without increasing the energy requirements of the overall system.

SUMMARY OF THE INVENTION

The present invention is an autoclave system which uses the exhaust gas of a turbine to heat an autoclave. The exhaust gas of the turbine is approximately 1200° F., low enough to be coupled to the heater coils of the autoclave. The output shaft of the turbine may be coupled to a generator that drives the autoclave motor and other subsystems. The output shaft of the turbine may also be coupled, either directly or through the generator, to the compressors of a nitrogen processing plant. The processed nitrogen can be introduced to the autoclave to reduce the risk of fires. The turbine based system provides an autoclave which is significantly more energy efficient than systems in the prior art. The turbine also allows a nitrogen processing plant to be coupled to an autoclave without significantly increasing the energy requirements of the overall system.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
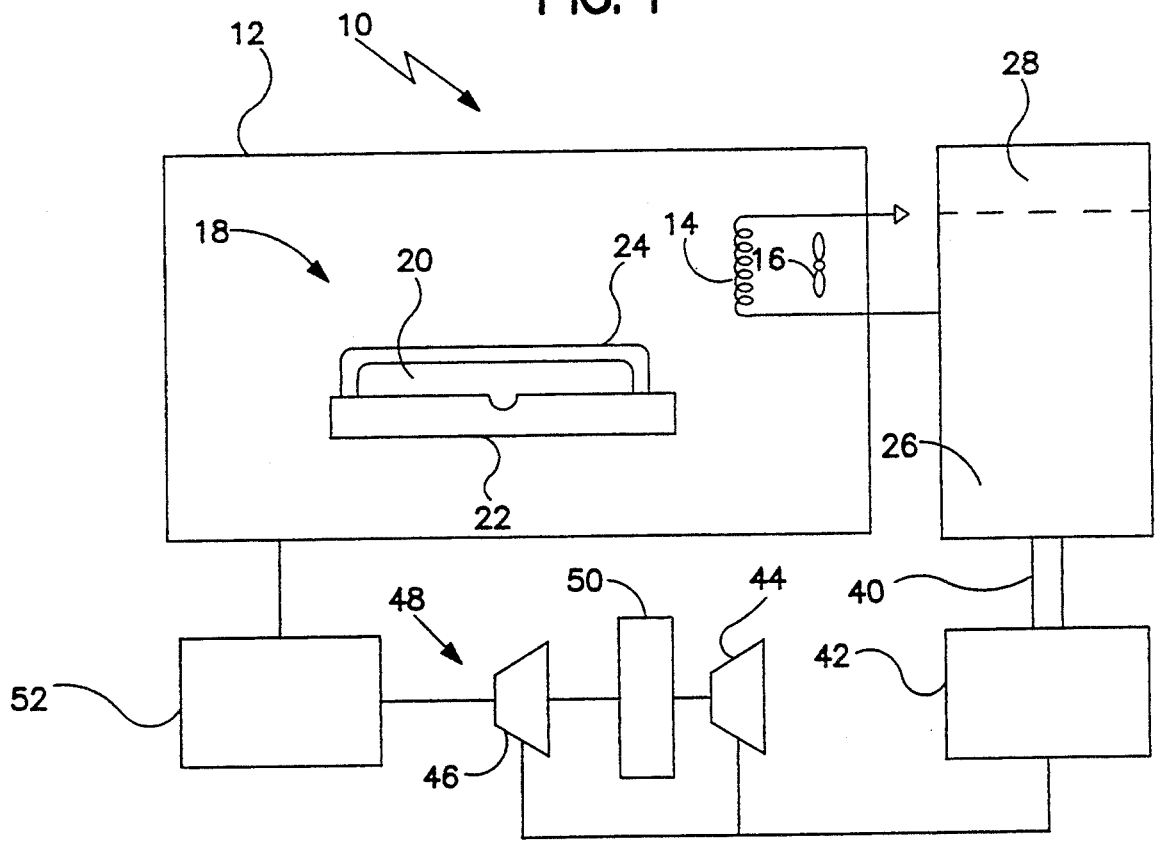
FIG. 1 is a schematic of an autoclave system of the present invention.

Referring to the drawings more particularly by reference numbers, FIG. 1 shows a schematic of an autoclave system 10 of the present invention. The system includes an autoclave tank 12. The autoclave includes a heater coil 14 adjacent to a fan 16 located within an inner chamber 18 of the tank 12. The autoclave tank 12 is typically used to form composite materials 20 under elevated temperatures and pressures. A typical autoclave cycle includes placing the material 20 onto a tool 22 and then covering the material 20 with a flexible bag 24. A vacuum is then pulled in the bag 24 to remove impurities under the bag 24. The inner chamber 18 is then heated and pressurized until the composite material is cured and formed onto the tool 22.

The heat is provided to the inner chamber 18 from a hot gas that flows through the coil 14. The hot gas flows from the output port of a turbine 26. The turbine 26 has a combustion chamber 28 which produces a hot gas that passes through the blades (not shown) of the turbine 26. The exhaust gas from the turbine blades is directed to the heater coil 14, where heat within the hot gas is transferred to the inner chamber 18 by the fan 16. In the preferred embodiment, the turbine is a gas turbine engine 26 sold by Pratt & Whitney under the designation ST6L-81 ("81"). The exhaust gas temperature of the 81 turbine is between 900° to 1200° F., a temperature low enough to meet the operating requirements of the heater coil 14. The present invention does not require excess air flow as does autoclave systems in the prior art. The energy efficiency of the combustion chamber of the autoclave system is therefore higher than systems in the prior art. In the preferred embodiment, water is injected into the combustion chamber 28 to reduce the nitrogen oxide emissions of the turbine 26.

Figure 2:
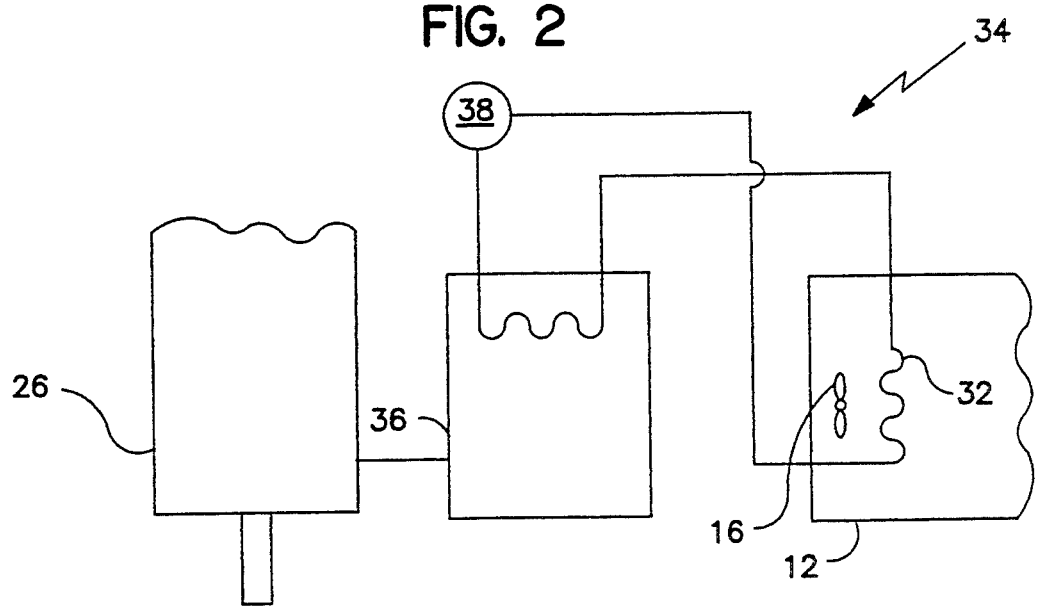
FIG. 2 is a schematic of an alternate embodiment of the system.

FIG. 2 shows an alternate embodiment, wherein the output gas of the turbine 26 is used to heat a secondary fluid that flows through the heater coils 32 of a separate closed subsystem 34. The output gas heats the secondary fluid in element 36. The heated secondary fluid is pumped into the heater coils 32 of the autoclave tank 12 by pump 38. The secondary fluid is typically water or an oil. The water/oil is typically heated to a temperature of approximately 350° F. The large thermal capacitance of the secondary fluid is capable of transferring a sufficient amount of heat to the autoclave even at the lower temperature. This embodiment is particularly suitable for existing water and oil heated autoclaves.

Referring to FIG. 1, the combusted gas of the combustion chamber 28 also powers an output shaft 40 of the turbine 26. The energy of the output shaft 40 can be used for various applications. In one embodiment, the output shaft 40 is coupled an electrical generator 42.

The electrical generator 42 can provide power to the autoclave motor and the other electrical subsystems of the autoclave 10, thereby reducing the requirements for external power and energy efficiency of the overall system.

The generator 42 can also be coupled to the compressors 44 and 46 of a nitrogen processing plant 48, such as the processing plant disclosed in U.S. Pat. No. 5,122,318 issued to Bonet et al, which is hereby incorporated by reference. The processing plant 48 contains a membrane 50 that generates essentially pure nitrogen from air. The air is pushed through the membrane 50 by the compressor 44. The processed nitrogen is then pumped into a holding tank 52. The nitrogen from the holding tank 52 can be introduced into the inner chamber 18 of the autoclave to reduce the probability of a fire igniting within the tank 12.

As an alternate embodiment, the compressors 44 and 46 can be mechanically coupled directly to the output shaft 40 of the turbine 26. The generator 42 may also be connected to the output shaft 40 along with the compressors 44 and 46. The generator 42 can provide power to the autoclave motor and the other subsystems of the autoclave.

As another embodiment, the turbine 26 can be coupled to the nitrogen processing plant 48 and not the autoclave tank 12. The exhaust gas from the turbine 26 can be used for some other cogeneration application. In this embodiment, the turbine 26 provides an efficient means for powering the compressors 44 and 46, and the option for additional cogeneration.

The turbine of the autoclave system provides the multiple functions of, increasing the energy efficiency of the combustion chamber, providing additional power that can be utilized to drive other subsystems and thus lowering the power consumption of the overall system, and allowing a nitrogen processing plant to be coupled to the autoclave without increasing the power requirements of the system. The preset invention thereby provides an autoclave system that is both efficient and safe.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An autoclave system, comprising:
   a turbine that Generates an output gas with a temperature between 900°–1200° F.;
   an autoclave that has an inner chamber; and,
   a heat exchanger coupled to said autoclave and said turbine such that said output gas of 900°–1200° F. flows through said heat exchanger and raises a temperature of said inner chamber.

2. The system as recited in claim 1, further comprising a generator coupled to an output shaft of said turbine.

3. The system as recited in claim 1, further comprising a heater coil that is located within said inner chamber, and a secondary fluid that is heated by said output gas and which flows through said heater coil.

4. The system as recited in claim 3, wherein said secondary fluid is water.

5. An autoclave system, comprising:
   an autoclave with an inner chamber;
   a compressor that generates a flow of air;
   a membrane that is in fluid communication with said autoclave inner chamber and said compressor, wherein said membrane generates a flow of nitrogen from the air provided by said compressor;
   a generator;
   a turbine that powers said generator and said compressor, said turbine generates an output gas with a temperature between 900°–1200° F.; and,
   a heat exchanger coupled to said autoclave and said turbine such that said output gas of 900°–1200° F. flows through said heat exchanger and raises a temperature of said inner chamber.

6. The system as recited in claim 5, wherein said compressor is coupled to an output shaft of said turbine.

7. The system as recited in claim 5, further comprising a second compressor that pumps said nitrogen to a holding tank.

* * * * *